United States Patent
Ono et al.

(10) Patent No.: US 6,539,272 B1
(45) Date of Patent: Mar. 25, 2003

(54) ELECTRIC DEVICE INSPECTION METHOD AND ELECTRIC DEVICE INSPECTION SYSTEM

(75) Inventors: Makoto Ono, Yokohama (JP); Hisafumi Iwata, Hayama-machi (JP); Kazunori Nemoto, Akishima (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/494,939

(22) Filed: Feb. 1, 2000

(30) Foreign Application Priority Data

Feb. 1, 1999 (JP) .......................... 11-023945

(51) Int. Cl.[7] ............................................. G06F 19/00
(52) U.S. Cl. ........................................ 700/110; 702/84
(58) Field of Search ................... 700/110, 109, 700/108; 382/56, 54; 702/33–40, 81–84

(56) References Cited

U.S. PATENT DOCUMENTS

| | | | |
|---|---|---|---|
| 5,598,341 A | 1/1997 | Ling et al. | 700/110 |
| 5,754,432 A * | 5/1998 | Komatsuzaki et al. | 700/110 |
| 5,971,586 A * | 10/1999 | Mori | 700/108 |
| 6,240,329 B1 * | 5/2001 | Sun | 700/110 |
| 6,259,960 B1 * | 7/2001 | Inokuchi | 700/110 |
| 6,265,232 B1 * | 7/2001 | Simmons | 438/14 |
| 6,314,379 B1 * | 11/2001 | Hu et al. | 702/81 |
| 6,324,481 B1 * | 11/2001 | Atchison et al. | 702/84 |

FOREIGN PATENT DOCUMENTS

| | | |
|---|---|---|
| JP | 08162510 | 6/1996 |
| JP | 09074056 | 3/1997 |

OTHER PUBLICATIONS

"Modification of Poisson Statistics: Modeling Defects Induced by Diffusion", written by O. Paz, et al. IEEE Journal of solid–state Circuits vol. SC–12 pp. 540–546(1977).

"Clustered Defects in IC Fabrication: Impact of Process Control Charts" written by D.J. Friedman, et al. IEEE Transactions on Semiconductor Manufacturing vol. 4 No.1 pp. 36–42 (1991).

"Statistical Micro Yield Modeling" written by Allan Y. Wong. Semiconductor International pp. 139–148(1996).

* cited by examiner

*Primary Examiner*—Leo Picard
*Assistant Examiner*—Zoila Cabrera
(74) *Attorney, Agent, or Firm*—Antonelli, Terry, Stout & Kraus, LLP

(57) ABSTRACT

An analysis method includes one or more inspection steps for inspecting defects on a wafer, including an electrical inspection an step for inspecting electrical function of dies of the wafer, a determination step for determining whether each die is a good die or a bad die by using results obtained in the electrical inspection step, a calculation step for calculating the yield of dies without defects by using results obtained in the determination step, and an output step for outputting a result of the calculation step.

5 Claims, 6 Drawing Sheets

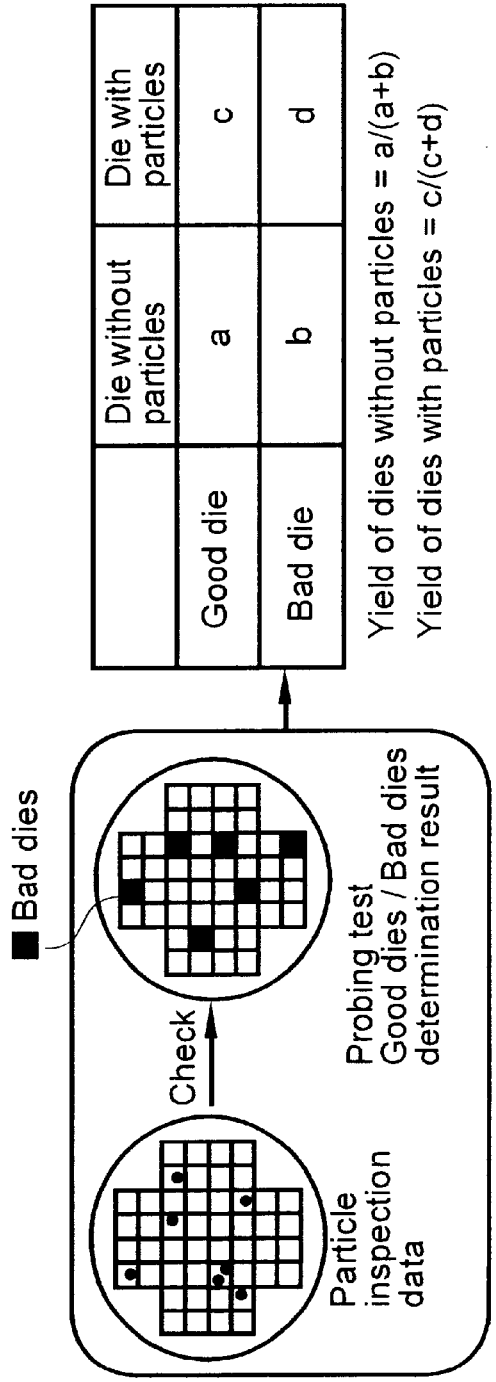

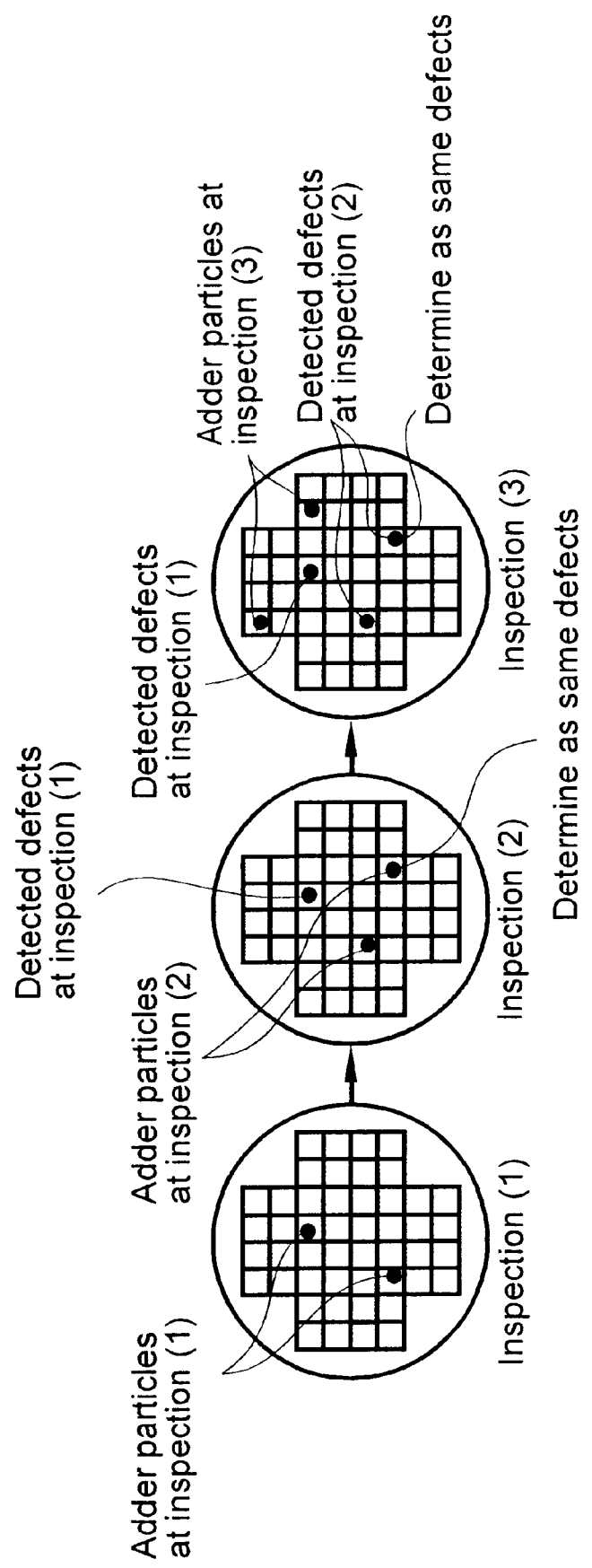

ELECTRIC DEVICE INSPECTION METHOD AND ELECTRIC DEVICE INSPECTION SYSTEM

BACKGROUND OF THE INVENTION

This invention relates to an inspection method and system to specify manufacturing processes in which measures should be taken against particles or pattern defects in the manufacture of a wafer. In this specification, particles and/or pattern defects are simply called defects.

Yield is a good dies ratio which is calculated using the results of a probing test, which is final electrical test in the process of manufacture of a wafer. That is, yield is a ratio of good dies to all dies of a wafer. To improve yield, it's important to calculate the yield impact of each manufacturing process and to take measures in the manufacturing process which has great yield impact.

Prior methods to quantify yield impact are as follows:

(1) A Correlation Analysis Between Yield and the Number of Defects

In this method, particle inspection or pattern defect inspection is performed every time a layer is formed on a wafer, and then the correlation analysis between yield and the number of defects is calculated based on results of a particles inspection or pattern defect inspection (See FIGS. 4(a) and 4(b)). According to this method, users can determine yield impact statistically.

However, this method must be performed on the premise that defects occur randomly on the wafer and that the inspection results follow the Poisson distribution. As shown in FIG. 4(a), the situation wherein yield decreases as the number of defects increases is an ideal correlation relation between yield and the number of defects. The slope of correlation relation of FIG. 4(a) represents yield impact per single detect. On the other hand, as shown in FIG. 4(b), in the case wherein clustered defects occur or defects concentrate at one area in a wafer due to equipment problems, the correlation relation between yield and the number of defects becomes indistinct, or in the worst case, the yield is likely to increase as the number of defects increases. This situation is opposite that of the ideal correlation relation shown in FIG. 4(a).

Methods for solving these problems are disclosed in the papers "Modification of Poisson statistics: Modeling defects induced by diffusion" written by O. Paz et al in the IEEE Journal of solid-state Circuits, vol. SC-12, pp. 540–546 (1977), and "Clustered Defects in IC Fabrication: Impact on Process Control Charts" written by D. J. Friedman et al in the IEEE Transactions on Semiconductor Manufacturing, vol. 4, No. 1 (1991). However, these prior methods can't take measures against false detection by an inspection tool.

And, in the paper "Statistical Micro Yield Modeling" written by Allan Y. Wong, in Semiconductor International, November, 1996, pp. 139–148, yield elements are resolved into systematic elements and random elements, and then the correlation relation of each element, between yield and the number of defects is analyzed. However, this prior method also can't take measures against false detection by an inspection tool.

(2) Kill Ratio Analysis Method

This method is disclosed in the paper "Yield Monitoring and Analysis in semiconductor manufacturing" written by S. Hall et al in the SEMICON KANSAI '97, ULSI technical seminar, pp. 4/42–4/47, (1997). As shown in FIG. 5, particle inspection or pattern defect inspection are performed every time each layer is formed on a wafer, and then the number of good dies a, c and the number of bad dies b, d are calculated based on the result of the final test(probing test). The value "a" is the number of good dies in the dies without particles. The value "b" is the number of bad dies in the dies without particles. The value "c" is the number of good dies in the dies with particles. The value "d" is the number of bad dies in the dies with particles. After this calculation, the yield of the dies without defects and the yield of the dies with defects are calculated, and the kill ratio of each layer is also calculated. According to the kill ratio obtained by this method, users can determine the number of bad dies which contain by defects. And, according to this method, the yield impact can be calculated without influence from process margin failure, such as process size and film thickness. However, this prior method also can't take measures against false detection by an inspection tool.

(3) Critical Area Analysis Method

This is a method to determine kill ratio depending on the area in the die by checking the a CAD data of circuit pattern with the size or position of defects. The method of determining kill ratio is disclosed in the paper "Modeling of defects in integrated circuit photolithographic patterns" written by C. H. Stapper in the IBM Journal of Research and Development, Vol. 28, No. 4, July, 1984, pp. 461–475, and in the paper "Modeling the Critical Area in Yield forecasts" written by A. V. FerrisPrabhu in the IEEE Journal of Solid-state Circuits, Vol. SC-20, No. 4, August, 1985, pp. 874–877. U.S. Pat. No. 5,598,341 discloses a yield control system using a critical area analysis method. This method can analyze more accurately than both the correlation analysis method and the kill ratio analysis method because it uses a circuit pattern. However, this prior method also can't take measures against false detection by an inspection tool and clustered defects.

False detection by an inspection tool means that non-real particles or nonreal pattern defects are, detected by the inspection tools as real particles or real pattern defects. For example, in case a film condition on a wafer is different from a normal film condition, if the sensitivity of the inspection tools is high, the film condition is likely to be detected as real particles or real pattern defects. And, if the lighting of the inspection tool changes value, the inspection tool is likely to detect non-real particles or non-real pattern defects as real particles or real pattern defects.

As mentioned above, the prior art can't take measures against false detection by inspection tools.

SUMMARY OF THE INVENTION

As mentioned above, the prior art can't take measures against false detection by inspection tools. Therefore, it is difficult to quantify yield impact acolirately by using the prior yield impact quantification methods because the prior methods are influenced by clustered defects, peculiar detect distribution on a wafer, false detection by inspection tools, and a disturbance such as process margin failure.

And, the prior methods require extraction of adder defects. As shown in FIG. 6, adder defects are defects which have occurred on a wafer newly. For example, in FIG. 6, detected defects which are detected at first inspection (1) are adder defects of inspection (1). Next, at inspection (2), the detected defects which are detected at inspection (1) are taken from detected defects which are detected at inspection (2), and then the result of this calculation becomes adder defects of inspection (2). Next, at inspection (3), detected defects which are detected at inspection (1) and detected defects which are detected at inspection (2) are taken from detected defects which are detected at inspection (3), and then the result of this calculation becomes adder defects of inspection (3). For the remainder of the inspection (4~), the same calculation is performed to calculate adder defects of each inspection step.

However, extraction of adder defects is influenced by reproductivity of the X-Y stage of the inspection tool or alignment error. And, cluster defects are likely to be detected differently at each of the inspection steps; especially, the size of the cluster defects will be detected differently at each of the inspection steps. Therefore, it is difficult to check one layer's defects with another layer's defects correctly.

The purpose of the invention is to quantify yield impact accurately, especially to quantify yield impact accurately without extraction of adder defects.

To achieve the purpose of the invention, the manufacturing line is controlled in accordance with the amount of yield impact of dies without defects. This method isn't influenced by the number of defects, the size of the defects, clustered defects, peculiar defect distribution on a wafer, false detection by inspection tools, and process margin failure. And, this method doesn't need to extract adder defects.

The analysis method comprises one or more inspection steps for inspecting defects on a wafer, including an electrical inspection step for inspecting an electrical function of dies of the wafer, a determination step for determining whether each die is a good die or a bad die by using the results of the electrical inspection step, a calculation step for calculating the yield of dies without defects by using the results of the determination step, said defects being cumulative defects which have been detected by the inspection steps, and an output step for outputting the result of the calculation step.

The analysis method comprises one or more inspection steps for inspecting defects on a wafer, including an electrical inspection step for inspecting an electrical function of dies of the wafer, a determination step for determining whether each die is a good die or a bad die by using the results of the electrical inspection step, a calculation step for calculating the yield of dies without defects by using the results of the determination step and an amount of yield impact between inspection steps, and an output step for outputting the result of the calculation step.

The analysis system comprises one or more inspection tools to inspect defects on a wafer, including a probing tester to inspect the electrical function of dies of the wafer, and an analysis machine to determine whether each die is a good die or a bad die by using the results provided by the probing tester and to calculate the yield of dies without defects by using the results of the determination as to whether each die is a good die or a bad die and to output result of the calculation, said defects being cumulative defects which have been detected by the inspection steps.

The analysis system comprises one or more inspection tools to inspect defects on a wafer, including a probing tester to inspect the electrical function of dies of the wafer, and an analysis machine to determine whether each die is a good die or a bad die by using the results provided by the probing tester and to calculate the yield of dies without defects by using the results of the determination as to whether each die is a good die or a bad die and an amount of yield impact between inspection steps and to output the result of the calculation.

The analysis machine comprises a first memory unit to store inspection results which indicate defects on a wafer detected by one or more inspection tools, a second memory unit to store inspection results which indicate the electrical function of dies of the wafer provided by a probing tester, and processor to determine whether each die is a good die or a bad die by using the results provided by the probing tester and to calculate the yield of dies without defects by using the results of the determination as to whether each die is a good die or a bad die and to output the result of the calculation, said defects being cumulative defects which have been detected by the inspection steps.

An analysis machine comprises a first memory unit to store inspection results which indicate defects on a wafer detected by one or more inspection tools, a second memory unit to store inspection results which indicate the electrical function of dies of the wafer provided by a probing tester, and processor to determine whether each die is a good die or a bad die by using the results provided by the probing tester and to calculate the yield of dies without defects by using the results of the determination as to whether each die is a good die or a bad die and an amount of yield impact between inspection steps and to output the result of the calculation.

The yield of dies without defects represents the yield of dies without cumulative defects which have been detected by the inspection steps.

The amount of yield impact is calculated by the following formula:

An amount of yield impact=1−( yield of the dies without cumulative defects which have been detected until the defect inspection $(k-1)$)/(yield of the dies without cumulative defects which have been detected until the defect inspection $(k)$), $k=1, 2, 3, \ldots n$.

The result of the inspection step indicates defects which have been detected by a particle inspection tool or a pattern defect inspection tool.

The output step produces a list showing the inspection step in order of greatness of yield impact.

The first memory unit and second memory unit are the same memory unit.

According to this invention, users can determine easily the order of priority of steps in a manufacturing process which should be taken as measures against defects. As a result, this method isn't influenced by the number of defects, the size of the defects, clustered defects, a peculiar defect distribution on a wafer, false detection by inspection tools, and process margin failure.

BRIEF DESCRIPTION OF THE DRAWINGS

FIG. 5 is a diagram showing an example of a kill ratio calculation method.

FIG. 6 is a diagram showing an example of an adder defect detection method.

DESCRIPTION OF PREFERRED EMBODIMENT

Preferred embodiments of the present invention will be described with reference to drawings.

Figure 1:
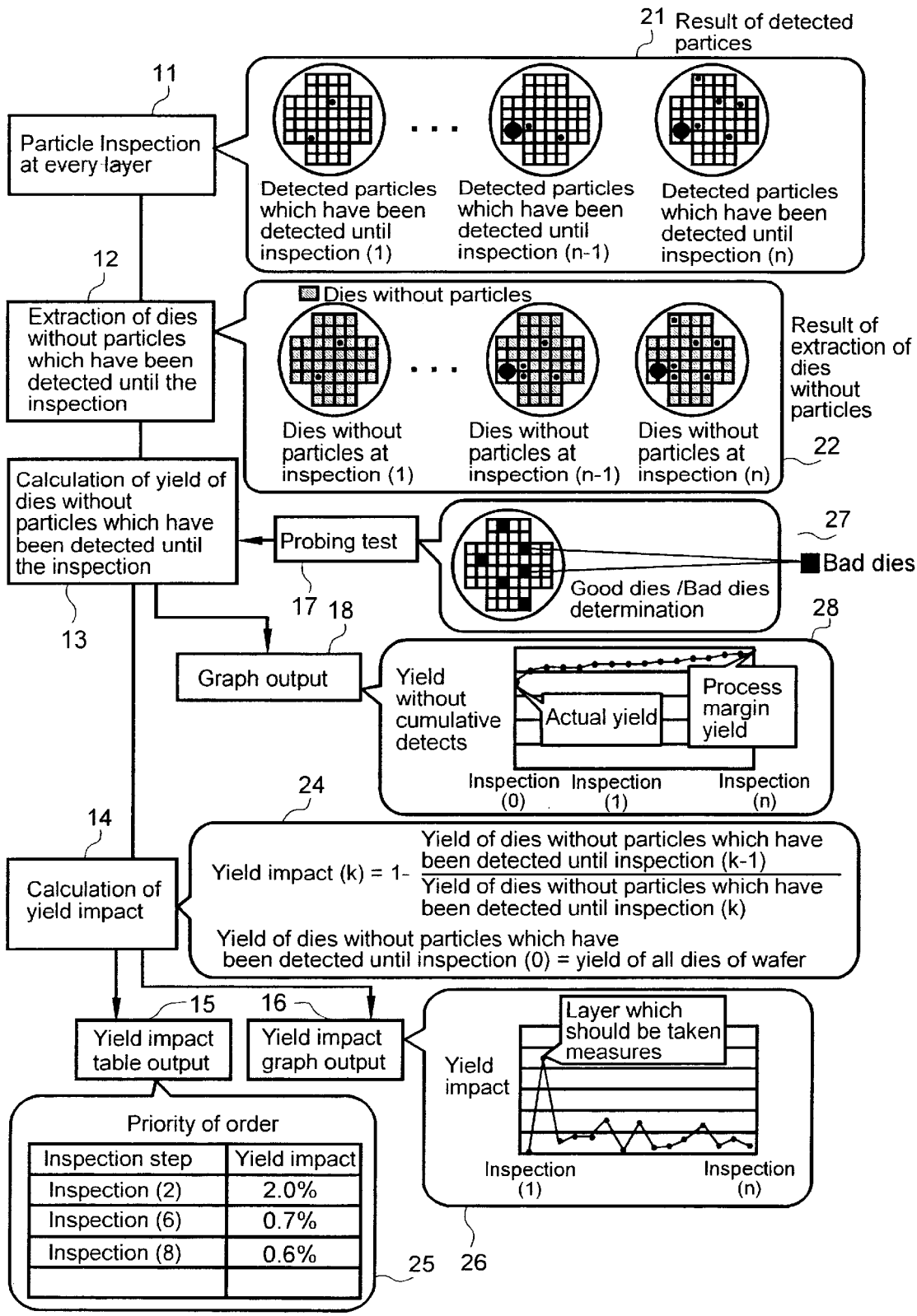
FIG. 1 is a flow chart showing an example of an electric device control method.
Figure 2:
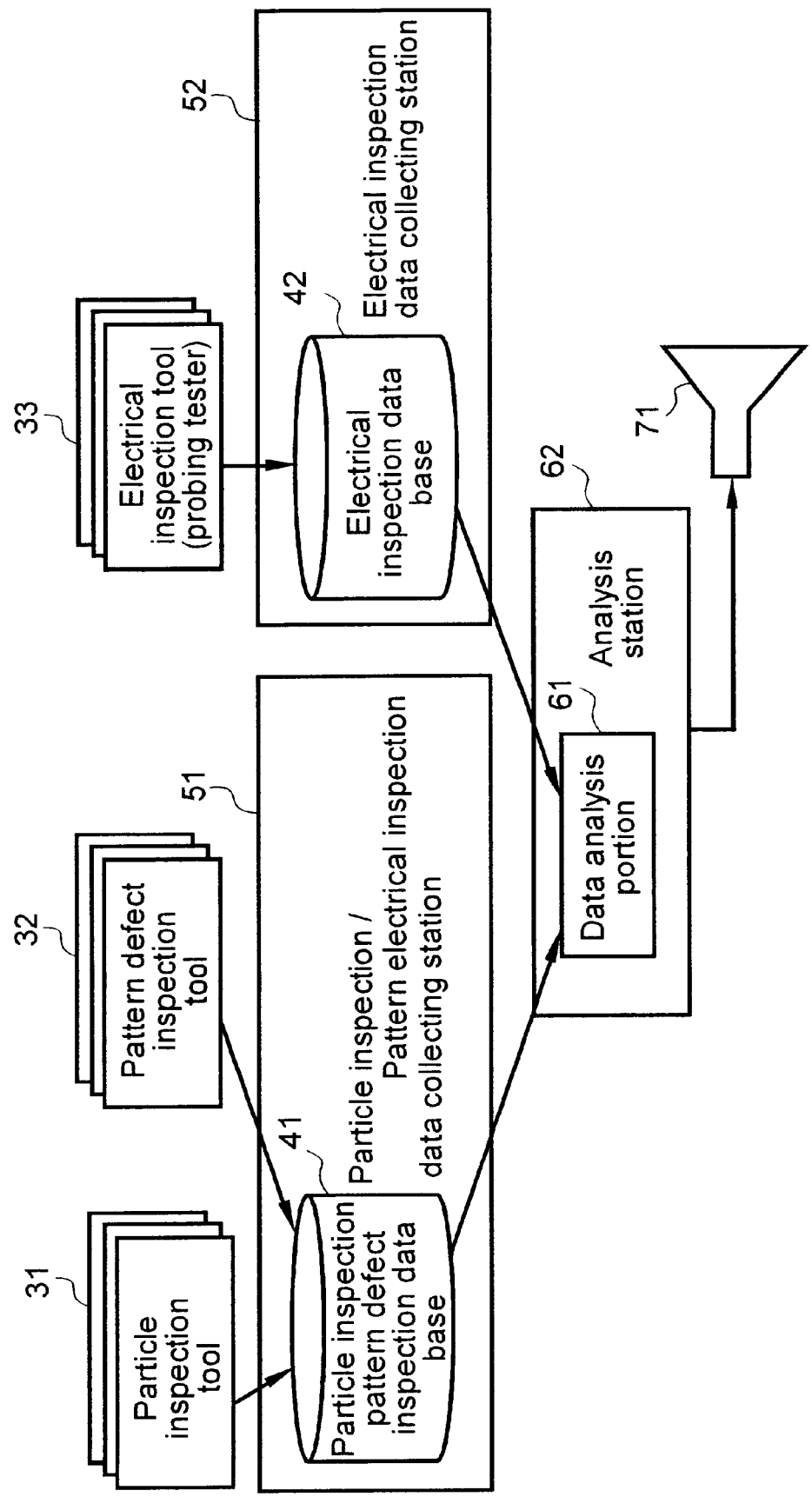
FIG. 2 is a block diagram showing an example of a system which performs the method illustrated in FIG. 1.

FIG. 1 is a flow chart showing an example of an electric device manufacturing control method, especially applied to a semiconductor wafer manufacturing line to search the manufacturing process to determine which measures are to be taken to avoid defects. FIG. 2 is a block diagram showing an example of a system which is used to carry out the method of FIG. 1.

In FIG. 2, the system has particle inspection tools 31, pattern defect inspection tools 32, a probing tester 33, a particle/pattern defect inspection database 41, an electrical inspection database 42, a particle/pattern data collecting station 51, an electrical inspection data collecting station 52, a data analysis portion 61, an analysis station 62.

In FIG. 1 and FIG. 2, at least one particle inspection tool 31 and/or at least one pattern defect inspection tool 32 are provided. The particle inspection tool 31 or pattern defect inspection tool 32 inspects particles or pattern defects every time each layer of semiconductor wafer is formed. In connection with this embodiment, we will describe an example wherein the particle inspection tool 31 is used to detect particles on a wafer.

First, when one layer of semiconductor wafer is formed, the particle inspection tool 31 inspects the wafer (step 11). The particle inspection result 21 shown in FIG. 1 represents the results of particle inspection. The particle inspection (1) is the first particle inspection, the particle inspection (2) is the second particle inspection, ... particle inspection (n) is $n^{th}$ particle inspection. The large circles in FIG. 1 represent semiconductor wafers, and the squares on the circles represent dies, and black marks represent detected particles. Each inspection result is stored in order in the particle/pattern defect inspection database 41 in FIG. 2. This particle inspection tool 31 has the function of projecting light on a layer formed on the semiconductor wafer, function of detecting scattered light, a function of judging defects from the strength of the scattered light, and a function of detecting the position of detected defects.

After the final particle inspection (n) is performed, electrical inspection is performed by the probing tester 33 to determine whether each die is a good die or not. This inspection corresponds to step 17 of FIG. 1. The good/bad determination result 27 shows good dies (white mark) and bad dies (black mark). This determination result is stored in the electrical inspection database 42.

After the particle inspection result 21 of each layer of the same semiconductor wafer has been stored in the particle/pattern defect inspection database 41 and the good/bad determination result 27 has been stored in the electrical inspection database 42, as the occasion demands, the particle inspection result 21 and the good/bad determination result 27 are read from analysis station 62. At the data analysis portion 61 of the analysis station 62, step 12 and step 13 are carried out.

At step 12, the dies(the dies without defects), in which no particles have been detected in the particle inspection, are extracted from the particle inspection results. The dies without defects are extracted for the inspection result of every layer. That, is, at the particle inspection (k), the dies (the dies without defects), in which no particles have been detected in the particle inspections (1) to the particle inspection (k), are extracted from particle inspection results 21. And, the dies without defects which have been detected until the particle inspections (1), the dies without defects which have been detected until the particle inspection (n−1), and the dies without defects which have been detected until the particle inspection (n) are color coded at the extraction results 22. The dies without defects which have been detected until the particle inspections (1) are those dies in which no particles have been detected in the first particle inspection. The dies without defects which have been detected until the particle inspection (n) are those dies in which no particles have been detected until the particle inspection (n). As the inspection progresses, the number of the dies without deferts decreases or keeps constant.

Next, at step 13, the yield of the dies without defects is calculated by using the extraction result 22 and the determination result 27. For example, in case of the dies in which defects have been detected in particle inspections (1), which corresponds to the extraction result 221, all dies except 3 dies with defects are considered to determine whether they are a good die or bad die according to the good/bad determination result 27, and the yield of the dies without defects is calculated. This yield is called the yield of dies without defects which have been detected until particle inspection (k). k=1, 2, 3 ... n.

Next, at step 14, the yield impact of each manufacturing process are calculated. Yield impact (k) between the particle inspection (k−1) and the particle inspection (k) is calculated as follows.

Yield impact $(k)1=($ yield of the dies without defects which have been detected until the particle inspection $(k-1))/$(yield of the dies without defects which have been detected until the particle inspection $(k)$), $k=1, 2, 3 \ldots n$. (1)

Yield of the dies without defects which have been detected until the particle inspection (0) is calculated from the yield of all dies, because there are no dies with defects.

As the manufacturing process proceeds, the number of dies with cumulative defects increases or doesn't change. Therefore, as the manufacturing process proceeds, the yield of the dies without defects which have been detected until the particle inspection (k) increases, because the number of dies without defects will decrease or not change. The relationship of the yield impact is as follow:

0<yield of the dies without defects which have been detected until the particle inspection $(k-1))/$(yield of the dies without defects–which have been detected until the particle inspection $(k)$)$\leq 1$ (2)

In this case, the greater killer defects increase, the more this ratio goes to 0. Therefore, according to relationship (1), the greater killer defects increase, the greater the yield impact (k) becomes. Yield impact of each particle inspection can be understood quantitatively by calculating yield impact every time the particle inspection (k) is performed.

Next, at step 15, particle inspections are arranged in order of greatness of yield impact and are outputted as list 25. This list may be outputted through display 71 of FIG. 2 or may be outputted through printers. According to this list 25, the order of priority in which the manufacturing process should take measures against particles can be understood. Or, at step 16, the graph 26 showing the relation between yield impact and particle inspections also may be outputted through display 71 of FIG. 2 or may be outputted through printers. In the graph 26, particle inspections (2), (6), (8), ... exceed the standards. Therefore, in this case, measures should be taken in the manufacturing processes just before these particle inspections.

By the way, the yield of the dies without defects which have been detected until the particle inspection (k) is the yield of dies in which no particles have been detected until this particle inspection (k). Instead of calculating yield impact, as shown at step 18, the graph 28 showing the relation between the particle inspections and the yield of dies without defects at particle inspection (k), which were calculated by step 13, also may be outputted through display 71 of FIG. 2 or may be outputted through printers.

Yield of dies without defects at particle inspection (k) refers to the yield of dies in which no defects have been detected any defects until the particle inspection (k). For example, at the extraction result 222, which is one extraction result of the dies without defects 22, there are eight dies with defects which have been detected until this particle inspection (n−1). The eight dies are excluded and the yield based on the dies, except for the eight dies, on the wafer is calculated by checking with the good dies/bad dies determination results 27. This is the yield of dies without defects which have been detected until particle inspection (n−1). This is also the yield of dies without defects at particle inspection (n−1).

In the case of extraction result 222, when the next layer is formed on the virtual wafer which excludes virtually eight dies with defects and then the particle inspection (n) is performed, bad dies which are caused by particles don't occur unless some defects occur. And, the yield of the virtual wafer doesn't decrease from the yield of dies without defects at particle inspection (n−1) unless bad dies caused by process margin failure, such as failure of size or film thickness, occur at the time when the next layer is formed. However, when bad dies which are caused by particles or process margin failure occur, the yield of the virtual wafer will decrease. Therefore, generally speaking, the yield of dies without defects at the particle inspection (k) is a maximum yield of the virtual wafer which has only dies without defects.

Yield of dies without defects at the particle inspection (k) increases suddenly when the detected defects at particle inspection (k) increase suddenly. Therefore, the sharper the slant of the line graph is in the graph 28, the greater will be the defects likely to occur at that time. In this case, the particle inspection (k) is supposed to influence the yield greatly.

As mentioned above, the yield impact of each manufacturing process can be indicated quantitatively by making a graph of the yield which has determined until particle inspection (k), k=1, 2, 3 . . . n.

In graph 28, the yield of dies without defects at the particle inspection (0) is calculated from the particle to inspection result of all dies and the good dies/bad dies determination results 27 of all dies. And, the yield of dies without defects at particle inspection (n) is the yield based on bad dies which were caused by process margin failure, because bad dies which were caused by particles are excluded.

As mentioned above, this system doesn't use adder defects which are used in the prior art to control the manufacturing line. According to the above system, if a false detection by inspection tools occurs, the dies indicated by the false detection are excluded from the analysis of the object dies. Therefore, the yield impact can be calculated accurately without the influence of false detection by inspection tools. Therefore, the sensitivity of the inspection tool can also be turned up.

Figure 3:
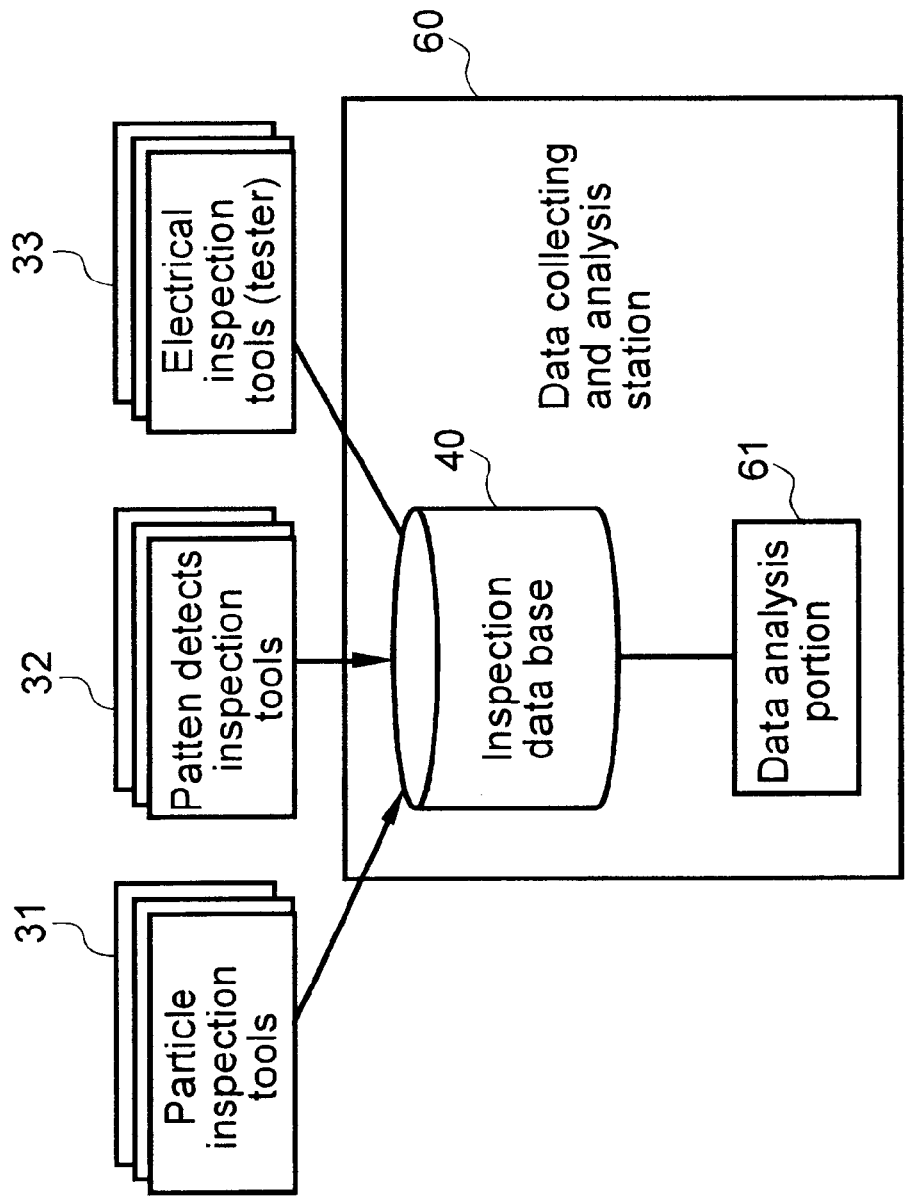
FIG. 3 is a block diagram showing another example of a system which performs the method of FIG. 1.
Figure 4B:
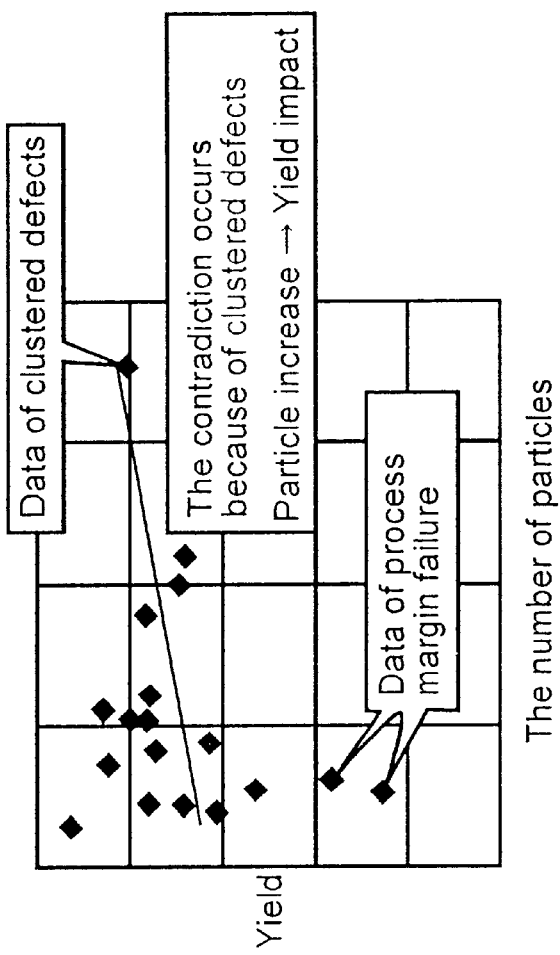
FIGS. 4(a) and 4(b) are diagrams showing an example of the correlation between the number of defects and yield.
Figure 4A:
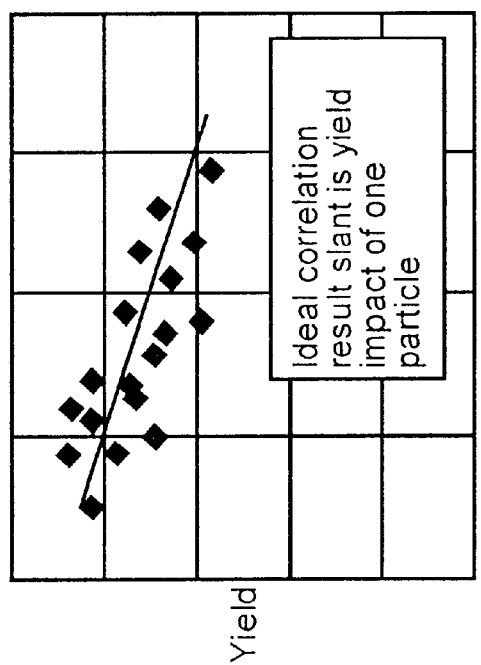

Further, the system structure shown in FIG. 2 is best used in a manufacturing line which involves mass production, and the structure shown in FIG. 3 is best used in a manufacturing line which doesn't involve mass production. In FIG. 3, the data collection function and the analysis function are performed at the same station 60, and each data item of the particle inspection, the pattern defect inspection, and the probing test are stored in the same data base 40.

This invention is not limited to only the above embodiments. For example, we explained the case in which inspection is carried out every time a layer was formed. However, if it's difficult to detect defects at the layer or it isn't important to inspect defects at the layer, the inspection isn't needed at the layer. According to this, the time to produce a semiconductor wafer can be shortened. And, instead of particle inspection, pattern defect inspection can be performed in the above embodiments. Of course, both the particle inspection and the pattern defect inspection can be performed in the above embodiments. In the pattern defect inspection, an abnormal portion of a circuit pattern is detected as a defect, and the size and location of the defect is detected.

In these embodiments, it is better to perform inspection with high sensitivity of detection. If the sensitivity of detection is high, the yield based on dies without defects which have been detected until final particle inspection right before the probing test is almost equal to the yield based on process margin failure, such as failure of size or film thickness.

As mentioned above, according to the invention, yield impact on the manufacturing process for an electrical device, such as semiconductor wafer, can be quantified. Therefore, the manufacturing process in which measures should be taken can be determined easily and effectively. And, the priority of the order in which measures should be taken can be determined. Therefore, this invention can contribute to failure analysis or yield improvement effectively.

And, according to the invention, yield based on process margin failure, which is caused by deviation in size or film thickness, can be calculated by using the inspection result of particle or pattern defects.

What is claimed is:

1. An analysis method including one or more inspection steps for inspecting defects on a wafer, comprising:

an electrical inspection step for inspecting an electrical function of dies of the wafer;

a determination step for determining whether each die is a good die or a bad die by using results obtained in said electrical inspection step;

a calculation step for calculating yield of dies without defects by using results obtained in said determination step and an amount of yield impact between inspection steps; and an output step for outputting a result of the calculation step;

wherein said yield of dies without defects is a yield of dies without cumulative defects which have been detected in the inspection step; and wherein said amount of yield impact is calculated by the following formula:

an amount of yield impact=1−(yield of the dies without defects which have been detected until the particle inspections−1))/(yield of the dies without defects which have been detected until the particle inspection(k)), k=1, 2, 3 . . . , n.

2. An analysis system comprising:

one or more inspection tools to inspect defects on a wafer;

a probing tester to inspect an electrical function of dies of the wafer; and an analysis machine to determine whether each die is a good die or a bad die by using results provided by the probing tester and to calculate yield of dies without defects by using the results of a determination whether each die is a good die or a bad die and an amount of yield impact between inspection steps and to output a result of the calculation;

wherein said yield of dies without defects are yield of dies without cumulative defects which have been detected by inspection; and wherein said amount of yield impact is calculated by the following formula:

an amount of yield impact=1−(yield of the dies without defects which have been detected until the particle inspections−1))/(yield of the dies without defects which have been detected until the particle inspection ($k$)), $k$=1, 2, 3 . . . , $n$.

3. An analysis machine comprising:

a first memory unit to store inspection results indicating defects on wafer detected by one or more inspection tools;

a second memory unit to store, inspection results indicating an electrical function of dies of the wafer obtained by a probing tester; and a processor to determine whether each die is a good die or a bad die by using results produced by the probing tester and to calculate yield of dies without defects by using the results of a determination whether each die is a good die or a bad die and an amount of yield impact between inspection steps and to output a result of the calculation;

wherein said amount of yield impact is calculated by the following formula:

an amount of yield impact=1−(yield of the dies without defects which have been detected until the particle inspections−1))/(yield of the dies without defects which have been detected until the particle inspection($k$)), $k$=1, 2, 3 . . . , $n$.

4. The analysis machine according to claim 3, wherein said processor produces a list showing inspection results in order of greatness of yield impact.

5. The analysis machine according to claim 3, wherein said first memory unit and second memory unit are the same memory unit.

* * * * *